(12) United States Patent
Dubberke et al.

(10) Patent No.: US 7,538,227 B2
(45) Date of Patent: May 26, 2009

(54) PROCESS FOR STABILIZING 4-HALOPYRIDINES

(75) Inventors: Silke Dubberke, Flörsheim (DE); Javier Manero, Liederbach (DE)

(73) Assignee: Sanofi-Aventis Deutschland GmbH, Frankfurt am Main (DE)

( * ) Notice: Subject to any disclaimer, the term of this patent is extended or adjusted under 35 U.S.C. 154(b) by 771 days.

(21) Appl. No.: 11/035,142

(22) Filed: Jan. 13, 2005

(65) Prior Publication Data

US 2005/0165239 A1 Jul. 28, 2005

Related U.S. Application Data

(60) Provisional application No. 60/579,825, filed on Jun. 15, 2004.

(30) Foreign Application Priority Data

Jan. 13, 2004 (DE) .................. 10 2004 001 950

(51) Int. Cl.
*C07D 211/72* (2006.01)
(52) U.S. Cl. .................................... 546/345
(58) Field of Classification Search .................. 546/345
See application file for complete search history.

(56) References Cited

U.S. PATENT DOCUMENTS 3,703,521 A 11/1972 Boudakian
7,112,682 B2 * 9/2006 Weiberth et al. ............ 548/483

FOREIGN PATENT DOCUMENTS

EP 0287982 10/1988

OTHER PUBLICATIONS

H. J. Den Hertog et al., Decomposition Reactions Of 4-Nitropyridine, Recueil (1951, pp. 105-110, vol. 70).
J. P. Wibaut et al., The Polymerisation Of 4-Chloropyridine, Recueil (1959, pp. 593-603, vol. 78).
J. P. Wibaut et al., The Reaction of 4-Chloropyridine With Some Amines, Recueil (1961, pp. 309-312, vol. 80).
James L. Lyle et al., The Synthesis Of 4-Fluorolutidiness and 4-Fluoropyridine, Journal Of Heterocyclic Chemistry (1972, pp. 745-746, vol. 9, No. 3).
M. Chahma et al., Use of Pyrrole Anions as Nucleophiles in Electrochemically Induced SRN1 Reactions, Tetrahedron Letter (1991, pp. 6121-6124, vol. 32, No. 43).
Sameer Urgaonkar et al., Application Of a New Bicyclic Triaminophosphine Ligand in Pd-Catalyzed Buchwald-Hartwig Amination Reactions of Aryl Chlorides, Bromides, and Iodides, J. Org. Chem. (2003, pp. 8416-8423, vol. 68).

* cited by examiner

*Primary Examiner*—Janet L Andres
*Assistant Examiner*—Binta M Robinson
(74) *Attorney, Agent, or Firm*—Jiang Lin; Balaram Gupta

(57) ABSTRACT

The present invention relates to a process for stabilizing 4-halopyridines of the formula (I)

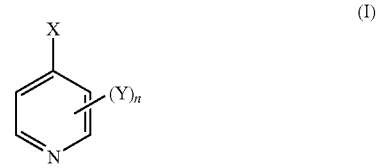

by adding a secondary and/or aliphatic or mixed aliphatic-aromatic tertiary amine, and mixtures comprising a compound of the formula (I) and a secondary and/or tertiary amine.

6 Claims, No Drawings

PROCESS FOR STABILIZING 4-HALOPYRIDINES

This application claims the benefit of U.S. Provisional Application No. 60/579,825, filed Jun. 15, 2004 and benefit of priority of Federal Republic of Germany Patent Application No. 102004001950.9-44, filed Jan. 13, 2004, both of which are incorporated herein by reference in their entirety.

BACKGROUND OF THE INVENTION

1. Field of the Invention

This invention relates to 4-halopyridines. In particular, this invention relates to a process for stabilizing 4-halopyridines.

2. Description of the Art

4-Halopyridines are compounds which are unstable in the course of storage at room temperature and are obtainable synthetically via methods known per se, for example by chlorinating the corresponding 4-hydroxypyridine with $PCl_5$ or $POCl_3$ (Wibaut & Broekmann, Recueil des Travaux Clinique des Pays-Bas et de la Belgique 7659, 78, 593-603). Impurities from the preparation process, especially residues of acid, lead to the decomposition of the 4-halopyridines and the formation of oligomeric products. One product formed in the case of 4-chloropyridine is the salt of the N-(4'-pyridyl)-4-chloropyridinium chloride dimer (Wibaut & Broeckmann, Recueil des Travaux Clinique des Pays-Bas et de la Belgique 1961, 80, 309-312).

Den Hertog et al. (Wibaut & Brockmann, Recueil des Travaux Clinique des Pays-Bas et de la Belgique 1951, 70, 105-111) state that 4-nitropyridine can be stabilized by the addition of 10% aqueous sodium bicarbonate solution, in which case 90% of 4-nitropyridine were still present unchanged at 60° C. after 12 hours.

According to Wibaut & Brockmann (Recueil des Travaux Clinique des Pays-Bas et de la Belgique 1961, 80, 309-312), 4-chloropyridine when mixed with primary amines $NH_2R$ (R=$CH_3$, $CH(CH_3)_2$, $C_{12}H_{25}$) or secondary amines $NHR'_2$ (R'=$CH_3$, n-$C_4H_9$), the formation of the corresponding (4-NHR)- and (4-$NR'_2$)-pyridines respectively is observed, while aliphatic tertiary or mixed aliphatic-aromatic tertiary amines (NEt$_3$, diethylaniline) did not react with 4-chloropyridine. 4-Chloropyridine forms an N-(4'-pyridyl)pyridinium salt with the aromatic tertiary amine pyridine. 4-Chloropyridine is currently commercially available only as the hydrochloride, in which the changed electronic conditions in the form of pyridinium salt stabilize the molecule.

SUMMARY OF THE INVENTION

The invention relates to a process for stabilizing 4-halopyridines of the formula (I)

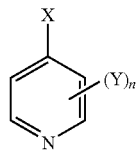

where
X is fluorine, chlorine, bromine or iodine,
Y is hydrogen, fluorine, chlorine, bromine, iodine, nitro, $NH_2$, ($C_1$-$C_4$)-alkyl, ($C_1$-$C_4$)-alkanoylamine, phenyl-($C_1$-$C_4$)-alkanoylamine, phenylcarbonylamine, ($C_1$-$C_4$)-alkylamine, di-($C_1$-$C_4$)-alkylamine, phenyl-($C_1$-$C_4$)-alkylamine, and n is 1 or 2, which comprises admixing one or more compounds of the formula (I) with one or more secondary and/or tertiary aliphatic or mixed aliphatic-aromatic amines.

The invention further relates to a mixture comprising
(a) one or more 4-halo-substituted pyridine derivatives of the formula (I)
where
X is fluorine, chlorine, bromine or iodine,
Y is hydrogen, fluorine, chlorine, bromine, iodine, nitro, $NH_2$, ($C_1$-$C_4$)-alkyl, ($C_1$-$C_4$)-alkanoylamine, phenyl-($C_1$-$C_4$)-alkanoylamine, phenylcarbonylamine, ($C_1$-$C_4$)-alkylamine, di-($C_1$-$C_4$)-alkylamine, phenyl-($C_1$-$C_4$)-alkylamine, and
n is 1 or 2, and
(b) one or more secondary amines and/or aliphatic or mixed aliphatic-aromatic tertiary amines, excluding a mixture comprising (a) 4-chloropyridine and (b) dimethylamine, di-(n-butyl)amine or triethylamine.

DETAILED DESCRIPTION OF THE INVENTION

In the process and in the mixture, in each case independently,
X is preferably Cl,
Y is preferably hydrogen or fluorine, and
n is preferably 1.

In the process and in the mixture, preference is given to using in each case one compound of the formula (I) and one amine.

Particular preference is given to a process or to a mixture in which the compound of the formula (I) is described by the formula (II) or (III):

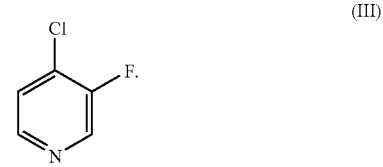

In the abovementioned process for stabilization, or in the abovementioned mixture, all secondary amines known to those skilled in the art, or preferably aliphatic or mixed aliphatic-aromatic tertiary amines, may be used.

A secondary amine is, for example, diisopropylamine, morpholine, pyrrolidine, piperidine, N,N-dicyclohexylamine, preferably diisopropylamine.

A tertiary aliphatic amine is, for example, N-methylmorpholine, ethyldiisopropylamine, N,N,N',N'-tetramethylethylenediamine (TMEDA), 1,5-diazabicyclo[4.3.0]-5-nonene (DBN); 1,8-diazabicyclo[5.4.0]-7-undecene (DBU), dicyclohexylethylamine, urotropine, preferably TMEDA, N-methylmorpholine and ethyldiisopropylamine.

A tertiary mixed aliphatic-aromatic amine is, for example, dimethylaminopyridine (DMAP), N,N-dimethylaniline, preferably DMAP.

In the process according to the invention, particular preference is given to using tetramethylethylenediamine (TMEDA), N-methylmorpholine and ethyldiisopropylamine.

The compounds of the formula (I) are useful as a starting material in the synthesis of pharmaceutical products. An example is the use of the compound (II) and (III) in the preparation of compounds which are described in the European patent applications EP 287 982 and can be employed for treating pain and depression. It is particularly advantageous when the 4-halopyridine starting material can first be stabilized and stored for a long period of time. Secondly, it is even more advantageous to have the 4-halopyridine free of impurities (for example of decomposition products) which might contaminate the pharmaceutical product. Finally, there should not be any safety risk especially involving any exothermically decomposable materials.

4-Chloro-3-fluoropyridine may be used, for example, in the preparation of the compound N-(3-fluoro-4-pyridinyl)-N-propyl-3-methyl-1H-indol-1-amine which finds use in the treatment of nerve damage. The chlorine substituent is replaced by an amine with addition of a base.

In the process according to the invention for stabilizing halopyridines or the mixture, preference is given to a content of up to 10%, preferably 5%, of amine.

The limited stability and the process according to the invention for increasing the stability is illustrated hereinbelow by way of an example using the compounds 4-chloropyridine and 4-chloro-3-fluoropyridine (4-ClFPy). The decomposition products of 4-ClFPy were investigated more precisely.

To elucidate the decomposition products, the solid which precipitated in the course of storage was filtered off with suction and subsequently separated by chromatography. To this end, the solid was dissolved in triethylamine and separated on silica gel using the eluent 4:1 ethyl acetate/ethanol. This gave two fractions: fraction 1 having $R_f=0.83$ and fraction 2 with $R_f=0.53$ in the eluent system mentioned. It was possible to elucidate the two fractions as the following dimerization/isomerization products:

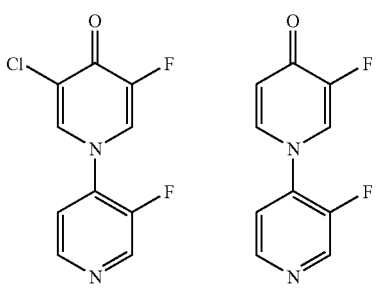

Two batches of 4-ClFPy having a different content of TMEDA were investigated for its storage stability at 20-25° C.

TABLE 1

| Batch No. | TMEDA content | Time | 4-ClFPy content | Purity (GC) |
|---|---|---|---|---|
| 1 | 2.15% | start of storage | 98.8% | 97.8% |
|  |  | +5 months | 98.2% | 97.9% |

TABLE 1-continued

| Batch No. | TMEDA content | Time | 4-ClFPy content | Purity (GC) |
|---|---|---|---|---|
| 2 | 0.47% | start of storage | 98.9% | 99.4% |
|  |  | +3 months | 100.9% | 99.5% |
|  |  | +9 months | 99.4% | 99.3% |

Within the range of measurement precision, the content of 4-chloro-3-fluoropyridine did not change over the period observed; the aliphatic tertiary amine TMEDA is thus capable of stabilizing 4-halo-substituted pyridines.

In order to verify the observed effect various other tertiary and secondary amines were further investigated, for e.g., using the amines triethylamine, N-methylmorpholine, ethyldiisopropylamine and diisopropylamine were each added in different mixtures (A: 10 μl to 5 ml; B: 10 μl to 1 ml) to a sample of 4-ClFPy, and the content of decomposition products after storage at room temperature was determined by means of gas chromatography (GC) (blank value: 0.097%):

TABLE 2

Stabilization of 4-ClFPy using various amines

| Amine | Amount | Period of storage at room temperature [days] | | | | | | |
|---|---|---|---|---|---|---|---|---|
|  |  | 3 | 10 | 17 | 24 | 31 | 59 | 80 |
|  |  | Content of decomposition products [%] | | | | | | |
| NEt₃ | A | 0.11 | 0.11 | 0.12 | 0.13 | 0.13 | 0.09 | 0.11 |
|  | B | 0.11 | 0.12 | 0.12 | 0.13 | 0.13 | 0.09 | 0.11 |
| N-methyl-morpholine | A | 0.11 | 0.12 | 0.12 | 0.12 | 0.13 | 0.07 | 0.10 |
|  | B | 0.11 | 0.12 | 0.12 | 0.12 | 0.13 | 0.15 | 0.10 |
| Et(i-Pr)₂N | A | 0.11 | 0.12 | 0.12 | 0.12 | 0.13 | 0.16 | 0.10 |
|  | B | 0.11 | 0.12 | 0.13 | 0.13 | 0.13 | 0.16 | 0.11 |
| (i-Pr)₂NH | A | 0.11 | 0.12 | 0.11 | 0.12 | 0.13 | 0.16 | 0.10 |
|  | B | 0.11 | 0.12 | 0.11 | 0.13 | 0.13 | 0.17 | 0.11 |
| TMEDA | A | 0.11 | 0.11 | 0.11 | 0.12 | 0.13 | 0.16 | 0.10 |
|  | B | 0.11 | 0.12 | 0.12 | 0.16 | 0.2 | 0.22 | 0.12 |

TABLE 3

Storage of 4-ClFPy (control experiment)

| Storage without amine [° C.] | Period of storage [days] | | | | | | |
|---|---|---|---|---|---|---|---|
|  | 3 | 10 | 17 | 24 | 31 | 59 | 80 |
| 20-25° C. | 0.13 | 0.21 | 0.34 | 0.71 | 1.5 | 0.72 | 0.41 |
| 0-5° C. | 0.11 | 0.14 | 0.13 | 0.17 | 0.22 | 0.38 | 0.17 |

In the course of storage at 20-25° C. in the control experiment, it was possible to detect solid at day 31; solid was likewise observed in the refrigerator sample (0-5° C.) from day 59. As soon as solid was present in the sample, it was no longer possible to take a homogeneous sample, so that the secondary component is underrepresented in the GC. In the subsequent measurements, lower values than before were thus found.

The variations in the preceding measurements are within the error range of the integration of the gas chromatograph. Even small amounts of amine are sufficient in order to stabilize 4-chloro-3-fluoropyridine. An example which can be mentioned is that of the two different concentrations of TMEDA; in the diluted case A, only 0.13% of TMEDA is detected. In comparison, the concentrated solution B indicates 0.61% of TMEDA. It is evident from the above-described experiments that the addition of a secondary amine and/or a tertiary aliphatic or mixed aliphatic-aromatic amine in the total concentration range of from about 0.05% to about 5.0%, preferably from about 0.1% to about 2.5%, stabilizes a 4-halopyridine derivative of the formula (I), preferably a compound of the formula (II) and (III).

EXAMPLE 1

Characterization of 4-chloro-3-fluoropyridine (III)

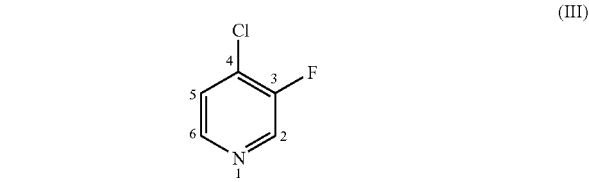

(III)

$^1$H NMR:

| | | |
|---|---|---|
| H2 8.5 ppm | J(H2-H6) = 0 Hz, J(H2-H5) = 0 Hz | 3JFH = 1 Hz |
| H5 7.4 ppm | J(H5-H6) = 5.3 Hz, J(H5-H2) = 0 Hz | 4JFH = 0 Hz |
| H6 8.3 ppm | J(H6-H2) = 0 Hz, J(H6-H5) = 5.3 Hz | 5JFH = 6.0 Hz |

$^{13}$C NMR:

| | | |
|---|---|---|
| C2 | 140 ppm | 2JFC = 23 Hz |
| C3 | 156 ppm | 1JFC = 259 Hz |
| C4 | 131 ppm | 2JFC = 15 Hz |
| C5 | 126 ppm | 3JFC = 2.3 Hz |
| C6 | 146 ppm | 4JFC = 5.7 Hz |

$^{19}$F NMR:

F3 131 ppm

EXAMPLE 2

Characterization of the Dimerization/Isomerization Products by NMR Chemical Shifts

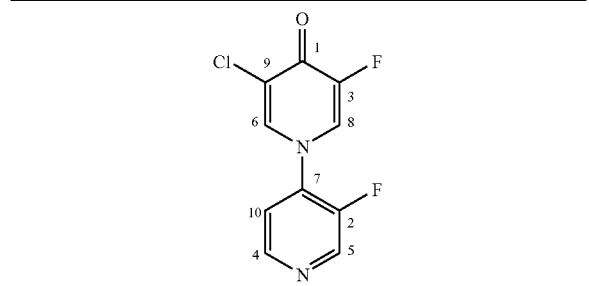

| $^1$H NMR | | $^{13}$C NMR | |
|---|---|---|---|
| H4 | 8.65 ppm, d | C1 | 164.06 ppm |
| H5 | 8.8 ppm, d | C2 | 151.76 ppm |
| H6 | 8.61 ppm, t | C3 | 151.58 ppm |
| H8 | 8.62 ppm, t | C4 | 147.29 ppm |
| H10 | 7.8 ppm, dd | C5 | 139.77 ppm |
| | | C6 | 137.8 ppm |
| | | C7 | 135.45 ppm |
| | | C8 | 127.51 ppm |
| | | C9 | 123.94 ppm |
| | | C10 | 121.06 ppm |

| $^1$H NMR | | $^{13}$C NMR | |
|---|---|---|---|
| H1 | 8.86 ppm, d | C1 | 139.56 ppm |
| H2 | 8.63 ppm, d | C2 | 147.09 ppm |
| H3 | 8.48 ppm, ddd | C3 | 126.97 ppm |
| H4 | 8.02 ppm, ddd | C4 | 139.13 ppm |
| H5 | 7.81 ppm, dd | C5 | 120.4 ppm |
| H6 | 6.53 ppm, dd | C6 | 118.3 ppm |
| | | C7 | 135.9 ppm |
| | | C8 | 153.38 ppm |
| | | C9 | 150.8 ppm |
| | | C10 | 168.95 ppm |

What is claimed is:

1. A process for stabilizing a compound of formula (III)

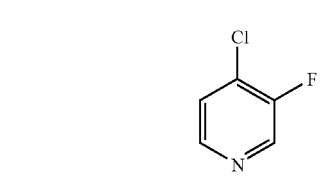

(III)

which comprises admixing the compound of formula (III) with one or more amines selected from the group consisting of secondary amines, tertiary aliphatic amines, and tertiary mixed aliphatic-aromatic amines.

2. The process as set forth in claim 1, wherein one amine is used.

3. The process as set forth in claim 2, wherein the content of secondary amine, tertiary aliphatic amine, or tertiary mixed aliphatic-aromatic amine is from about 0.05% to about 5.0%.

4. The process as set forth in claim 3, wherein the secondary amine is diisopropylamine, morpholine, pyrrolidine, piperidine or N,N-dicyclohexylamine.

5. The process as set forth in claim 3, wherein the tertiary aliphatic amine is
N-methylmorpholine, ethyldiisopropylamine,
N,N,N',N'-tetramethylethylenediamine (TMEDA), 1,5-diazabicyclo[4.3.0]-5-nonene (DBN), 1,8-diazabicyclo[5.4.0]-7-undecene (DBU), dicyclohexylethylamine or urotropine.

6. The process as set forth in claim 3, wherein the tertiary mixed aliphatic-aromatic amine is dimethylaminopyridine (DMAP) or N,N-dimethylaniline.

* * * * *